United States Patent [19]

Stetter et al.

[11] 4,338,119
[45] Jul. 6, 1982

[54] N-DIAZOLYLALKYL-HALOACETANILIDE COMPOUNDS AND HERBICIDAL COMPOSITIONS

[75] Inventors: Jörg Stetter; Klaus Ditgens, both of Wuppertal; Rudolf Thomas, Haan; Ludwig Eue, Leverkusen; Robert R. Schmidt, Cologne, all of Fed. Rep. of Germany

[73] Assignee: Bayer Aktiengesellschaft, Leverkusen, Fed. Rep. of Germany

[21] Appl. No.: 73,981

[22] Filed: Sep. 10, 1979

[30] Foreign Application Priority Data

Sep. 28, 1978 [DE] Fed. Rep. of Germany ..... 28422846

[51] Int. Cl.³ .................... A01N 9/22; C07D 271/06
[52] U.S. Cl. ........................................... 71/92; 71/91; 548/107; 548/128; 548/129; 548/131; 548/132; 548/133; 548/262; 548/265; 548/266; 548/269
[58] Field of Search ...................... 548/131, 132, 133; 71/92, 91

[56] References Cited

U.S. PATENT DOCUMENTS 4,243,408  1/1981  Chan ................................. 548/132

*Primary Examiner*—Donald G. Daus
*Assistant Examiner*—James H. Turnipseed
*Attorney, Agent, or Firm*—Felfe & Lynch

[57] ABSTRACT

Novel N-Diazolylalkyl-haloacetanilides of the formula

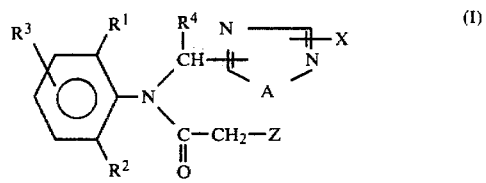

wherein
  A is oxygen, sulphur or the grouping >NR,
wherein
  R is hydrogen or alkyl,
  $R^1$ is hydrogen, alkyl or alkoxy,
  $R^2$ is hydrogen, alkyl, alkoxy or halogen,
  $R^3$ is hydrogen, alkyl, alkoxy or halogen,
  $R^4$ is hydrogen or alkyl,
  X is hydrogen, alkyl, halogen, alkoxy, alkylthio, haloalkyl, alkenyl, alkynyl, alkoxycarbonyl, dialkylamino, cyano, phenyl, substituted phenyl, phenoxy, substituted phenoxy, phenylthio or substituted phenylthio, and
  Z is halogen,
and in which the diazolyl radical is bonded via a carbon atom, and acid addition salts and metal salt complexes thereof.

30 Claims, No Drawings

N-DIAZOLYLALKYL-HALOACETANILIDE COMPOUNDS AND HERBICIDAL COMPOSITIONS

This invention relates to new N-diazolylalkyl-haloacetanilide compounds, to herbicidal compositions containing them, and to methods of combating weeds utilizing such compounds.

It is already known that 2,6-diethyl-N-methoxymethyl-chloroacetanilide can be used for selectively combating weeds (see R. Wegler, Chemie der Pflanzenschutz- und Schädlingsbekämpfungsmittel (Chemistry of Plant Protection Agents and Agents for Combating Pests), Vol. 5, page 255, Springer-Verlag (1977)). However, this compound is not always sufficiently active and its selectivity is not always completely satisfactory.

The present invention now provides, as new compounds, the N-diazolylalkyl-haloacetanilides of the formula

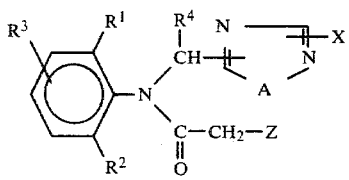 (I)

wherein

A is oxygen, sulphur or the grouping >NR. wherein R is hydrogen or alkyl, $R^1$ is hydrogen, alkyl or alkoxy, $R^2$ is hydrogen, alkyl, alkoxy or halogen, $R^3$ is hydrogen, alkyl, alkoxy or halogen, $R^4$ is hydrogen or alkyl, X is hydrogen, alkyl, halogen, alkoxy, alkylthio, haloalkyl, alkenyl, alkynyl, alkoxycarbonyl, dialkylamino, cyano, phenyl, substituted phenyl, phenoxy, substituted phenoxy, phenylthio or substituted phenylthio, and Z represents halogen, and the diazolyl radical is bonded via a carbon atom, and acid addition salts and metal salt complexes thereof.

The new N-diazolylalkyl-haloacetanilides of the formula (I) and the acid addition salts and metal salt complexes thereof have powerful herbicidal properties, in particular also selective herbicidal properties.

Preferably, in formula (I), A represents oxygen, sulphur or the grouping >NR,

R represents hydrogen or straight-chain or branched alkyl with 1 to 4 carbon atoms, $R^1$ represents hydrogen or straight-chain or branched alkyl or alkoxy with in either case 1 to 4 carbon atoms, $R^2$ and $R^3$, which are identical or different, each represent hydrogen, straight-chain or branched alkyl or alkoxy with in either case 1 to 4 carbon atoms, fluorine, chlorine or bromine, $R^4$ represents hydrogen or alkyl with 1 to 4 carbon atoms, X represents hydrogen, straight-chain or branched alkyl with 1 to 4 carbon atoms, straight-chain or branched alkoxy with 1 to 4 carbon atoms, straight-chain or branched alkylthio with 1 to 4 carbon atoms, alkoxycarbonyl with 1 to 4 carbon atoms in the alkoxy group, alkenyl or alkynyl with in either case 2 to 4 carbon atoms, fluorine, chlorine, bromine, 1 haloalkyl 1 with up to 2 carbon atoms and up to 5 identical or different halogen atoms (preferred halogens being fluorine, chlorine and bromine), dialkylamino with 1 to 4 carbon atoms in each alkyl part, cyano, optionally substituted phenyl, optionally substituted phenoxy or optionally substituted phenylthio, the substituent(s) on the three last-mentioned radicals being selected from halogen and alkyl with 1 or 2 carbon atoms, and Z represents chlorine, bromine or iodine.

The invention also provides a process for the preparation of an N-diazolylalkyl-haloacetanilide of the formula (I), or an acid addition salt or metal salt complex thereof, in which (a) an N-diazolylalkyl-aniline of the general formula

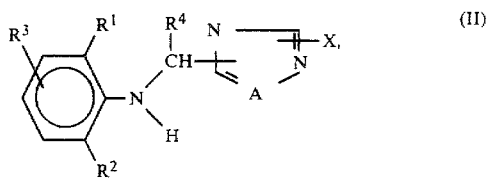 (II)

in which

A, $R^1$, $R^2$, $R^3$, $R^4$ and X have the meanings stated above, is reacted with a haloacetic acid chloride or bromide or anhydride of the formula $$Z-CH_2-CO-Cl(Br) \quad (IIIa)$$

or $$(Z-CH_2-CO)_2O \quad (IIIb),$$

in which

Z has the meaning stated above, in the presence of a diluent and if appropriate in the presence of an acid-binding agent, or (b) a haloacetanilide of the general formula

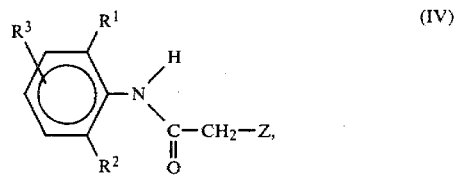 (IV)

in which $R^1$, $R^2$, $R^3$ and Z have the meanings stated above, is reacted with a diazolylalkyl derivative of the general formula

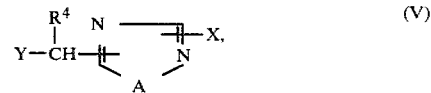 (V)

in which

A, $R^4$ and X have the meanings stated above and

Y represents halogen or the mesylate or tosylate radical, in the presence of an acid-binding agent and if appropriate in the presence of an organic diluent, and, if required, an acid or a metal salt is then optionally added onto the compound (I) prepared by variant (a) or variant (b) above.

Surprisingly, the possibilities of using the N-diazolylalkyl-haloacetanilides according to the invention, which have a very good herbicidal action, as agents for selectively combating weeds in important crop plants are better than those of using 2,6-diethyl-N-methoxymethylchloroacetanilide, which is known from the state of the art and is an active compound of high activity and the same type of action. The substances according to the invention thus represent a valuable enrichment of the art.

Particularly preferred N-diazolylalkyl-haloacetanilides of the formula (I) are those in which A represents oxygen, sulphur or the grouping >NR, R representing methyl, ethyl, propyl or butyl; $R^1$ represents hydrogen, methyl, ethyl, isopropyl, sec.-butyl, tert.-butyl, methoxy, ethoxy or isopropoxy; $R^2$ and $R^3$, which are identical or different, each represent hydrogen, methyl, ethyl, isopropyl, sec.-butyl, tert.-butyl, methoxy, ethoxy, isopropoxy, chlorine or bromine; $R^4$ represents hydrogen or methyl, X represents hydrogen, methyl, ethyl, n-propyl, isopropyl, n-butyl, sec.-butyl, tert.-butyl, allyl, propargyl, methoxy, ethoxy, isopropoxy, methylthio, ethylthio, isopropylthio, methoxycarbonyl, ethoxycarbonyl, fluorine, chlorine, bromine, chloromethyl, bromomethyl, dichloromethyl, trichloromethyl, trifluoromethyl, dimethylamino, ethylmethylamino, cyano, phenyl which is optionally substituted by chlorine and/or methyl, phenoxy which is optionally substituted by chlorine and/or methyl or phenylthio which is optionally substituted by chlorine and/or methyl; and Z represents chlorine or bromine.

The following compounds of the general formula (I) may be mentioned specifically, in addition to the compounds mentioned in the preparative examples given later in this text:

(I a)

| $R^1$ | $R^2$ | $R^3$ | $R^4$ | X |
|---|---|---|---|---|
| CH₃ | CH₃ | H | H | CH₃ |
| C(CH₃)₃ | H | H | H | CH₃ |
| CH₃ | H | 3-CH₃ | H | CH₃ |
| CH₃ | H | 5-CH₃ | H | CH₃ |
| CH₃ | OCH₃ | H | H | CH₃ |
| OCH₃ | OCH₃ | H | H | CH₃ |
| CH₃ | Cl | H | H | CH₃ |
| C(CH₃)₃ | Cl | H | H | CH₃ |
| C₂H₅ | C₂H₅ | H | H | H |
| CH₃ | C₂H₅ | H | H | H |
| CH₃ | CH₃ | H | H | H |
| C(CH₃)₃ | H | H | H | H |
| C₂H₅ | C₂H₅ | H | CH₃ | H |
| CH₃ | C₂H₅ | H | CH₃ | H |
| CH₃ | CH₃ | H | CH₃ | H |
| C(CH₃)₃ | H | H | CH₃ | H |
| CH₃ | C₂H₅ | H | CH₃ | CH₃ |
| C₂H₅ | C₂H₅ | H | CH₃ | CH₃ |
| CH₃ | CH₃ | H | CH₃ | CH₃ |
| CH₃ | H | 3-CH₃ | H | H |
| CH₃ | H | 5-CH₃ | H | H |
| CH₃ | OCH₃ | H | H | H |
| OCH₃ | OCH₃ | H | H | H |
| CH₃ | Cl | H | H | H |
| C(CH₃)₃ | Cl | H | H | H |
| C₂H₅ | CH₃ | H | H | C₂H₅ |
| C₂H₅ | C₂H₅ | H | H | C₂H₅ |
| CH₃ | CH₃ | H | H | C₂H₅ |
| C₂H₅ | CH₃ | H | H | Cl |
| C₂H₅ | C₂H₅ | H | H | Cl |
| CH₃ | CH₃ | H | H | Cl |
| C₂H₅ | CH₃ | H | H | Br |
| C₂H₅ | C₂H₅ | H | H | Br |
| CH₃ | CH₃ | H | H | Br |
| C₂H₅ | CH₃ | H | H | ⌬ |
| C₂H₅ | C₂H₅ | H | H | ⌬ |
| CH₃ | CH₃ | H | H | ⌬ |
| C₂H₅ | CH₃ | H | H | C₃H₇ |
| C₂H₅ | C₂H₅ | H | H | C₃H₇ |
| CH₃ | CH₃ | H | H | C₃H₇ |
| C₂H₅ | CH₃ | H | H | OCH₃ |
| C₂H₅ | C₂H₅ | H | H | OCH₃ |
| CH₃ | CH₃ | H | H | OCH₃ |
| C₂H₅ | CH₃ | H | H | SCH₃ |
| C₂H₅ | C₂H₅ | H | H | SCH₃ |
| CH₃ | CH₃ | H | H | SCH₃ |
| C₂H₅ | CH₃ | H | H | F |
| C₂H₅ | C₂H₅ | H | H | F |
| CH₃ | CH₃ | H | H | F |

(I b)

| $R^1$ | $R^2$ | $R^3$ | $R^4$ | X |
|---|---|---|---|---|
| CH₃ | CH₃ | H | H | CH₃ |
| C(CH₃)₃ | H | H | H | CH₃ |
| C₂H₅ | C₂H₅ | H | CH₃ | CH₃ |
| CH₃ | C₂H₅ | H | CH₃ | CH₃ |
| CH₃ | CH₃ | H | CH₃ | CH₃ |
| C(CH₃)₃ | H | H | CH₃ | CH₃ |
| CH₃ | H | 3-CH₃ | H | CH₃ |
| CH₃ | H | 5-CH₃ | H | CH₃ |
| CH₃ | OCH₃ | H | H | CH₃ |
| OCH₃ | OCH₃ | H | H | CH₃ |
| CH₃ | Cl | H | H | CH₃ |
| C(CH₃)₃ | Cl | H | H | CH₃ |
| C₂H₅ | C₂H₅ | H | H | H |
| CH₃ | C₂H₅ | H | H | H |
| CH₃ | CH₃ | H | H | H |
| C(CH₃)₃ | H | H | H | H |
| C₂H₅ | C₂H₅ | H | CH₃ | H |
| CH₃ | C₂H₅ | H | CH₃ | H |
| CH₃ | CH₃ | H | CH₃ | H |
| C(CH₃)₃ | H | H | CH₃ | H |
| CH₃ | H | 3-CH₃ | H | H |
| CH₃ | H | 5-CH₃ | H | H |
| CH₃ | OCH₃ | H | H | H |
| OCH₃ | OCH₃ | H | H | H |
| CH₃ | Cl | H | H | H |
| C(CH₃)₃ | Cl | H | H | H |
| CH₃ | C₂H₅ | H | H | C₂H₅ |
| CH₃ | CH₃ | H | H | C₂H₅ |
| C₂H₅ | C₂H₅ | H | H | n-C₃H₇ |
| CH₃ | C₂H₅ | H | H | n-C₃H₇ |
| CH₃ | CH₃ | H | H | n-C₃H₇ |
| CH₃ | C₂H₅ | H | H | i-C₃H₇ |
| C₂H₅ | C₂H₅ | H | H | i-C₃H₇ |
| CH₃ | CH₃ | H | H | i-C₃H₇ |
| C₂H₅ | C₂H₅ | H | H | n-C₄H₉ |
| CH₃ | CH₃ | H | H | n-C₄H₉ |
| CH₃ | C₂H₅ | H | H | n-C₄H₉ |
| C₂H₅ | C₂H₅ | H | H | t-C₄H₉ |
| CH₃ | CH₃ | H | H | t-C₄H₉ |
| C₂H₅ | C₂H₅ | H | H | ⌬ |
| CH₃ | C₂H₅ | H | H | ⌬ |
| CH₃ | CH₃ | H | H | ⌬ |
| C₂H₅ | C₂H₅ | H | H | Cl |
| CH₃ | C₂H₅ | H | H | Cl |

-continued

| R¹ | R² | R³ | R⁴ | X |
|---|---|---|---|---|
| CH₃ | CH₃ | H | H | Cl |
| C₂H₅ | C₂H₅ | H | H | OCH₃ |
| CH₃ | C₂H₅ | H | H | OCH₃ |
| C₂H₅ | C₂H₅ | H | H | OC₂H₅ |
| CH₃ | C₂H₅ | H | H | OC₂H₅ |
| C₂H₅ | C₂H₅ | H | H | —O—⟨phenyl⟩ |
| CH₃ | C₂H₅ | H | H | —O—⟨phenyl⟩ |

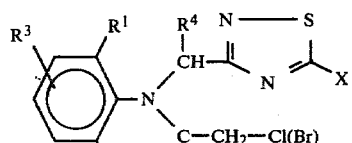  (I c)

| R¹ | R² | R³ | R⁴ | X |
|---|---|---|---|---|
| CH₃ | CH₃ | H | H | H |
| CH₃ | C₂H₅ | H | H | H |
| C₂H₅ | C₂H₅ | H | H | H |
| CH₃ | CH₃ | H | CH₃ | H |
| C₂H₅ | C₂H₅ | H | CH₃ | H |
| CH₃ | C₂H₅ | H | CH₃ | H |
| CH₃ | H | 3-CH₃ | H | H |
| CH₃ | H | 5-CH₃ | H | H |
| CH₃ | Cl | H | H | H |
| C(CH₃)₃ | Cl | H | H | H |
| CH₃ | OCH₃ | H | H | H |
| OCH₃ | OCH₃ | H | H | H |
| OCH₃ | C₂H₅ | H | H | H |
| OC₂H₅ | OC₂H₅ | H | H | H |
| CH₃ | CH₃ | H | H | CH₃ |
| CH₃ | C₂H₅ | H | H | CH₃ |
| C₂H₅ | C₂H₅ | H | H | CH₃ |
| C(CH₃)₃ | H | H | H | CH₃ |
| CH₃ | C₂H₅ | H | H | —⟨phenyl⟩ |
| C₂H₅ | C₂H₅ | H | H | —⟨phenyl⟩ |
| CH₃ | CH₃ | H | H | OCH₃ |
| CH₃ | C₂H₅ | H | H | OCH₃ |
| C₂H₅ | C₂H₅ | H | H | OCH₃ |
| C(CH₃)₃ | H | H | H | OCH₃ |
| CH₃ | CH₃ | H | H | SCH₃ |
| CH₃ | C₂H₅ | H | H | SCH₃ |
| C₂H₅ | C₂H₅ | H | H | SCH₃ |
| C(CH₃)₃ | H | H | H | SCH₃ |
| CH₃ | C₂H₅ | H | H | OC₂H₅ |
| C₂H₅ | C₂H₅ | H | H | OC₂H₅ |
| CH₃ | C₂H₅ | H | H | —O—⟨phenyl⟩ |
| C₂H₅ | C₂H₅ | H | H | —O—⟨phenyl⟩ |
| CH₃ | C₂H₅ | H | H | SC₂H₅ |
| C₂H₅ | C₂H₅ | H | H | SC₂H₅ |
| CH₃ | C₂H₅ | H | H | —S—⟨phenyl⟩ |
| C₂H₅ | C₂H₅ | H | H | —S—⟨phenyl⟩ |
| CH₃ | CH₃ | H | H | Cl |
| CH₃ | C₂H₅ | H | H | Cl |
| C₂H₅ | C₂H₅ | H | H | Cl |
| CH₃ | CH₃ | H | H | Br |
| CH₃ | C₂H₅ | H | H | Br |
| C₂H₅ | C₂H₅ | H | H | Br |
| CH₃ | CH₃ | H | H | N(CH₃)₂ |
| CH₃ | C₂H₅ | H | H | N(CH₃)₂ |
| C₂H₅ | C₂H₅ | H | H | N(CH₃)₂ |

-continued

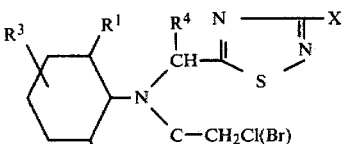  (Id)

| R¹ | R² | R³ | R⁴ | X |
|---|---|---|---|---|
| CH₃ | CH₃ | H | H | H |
| CH₃ | C₂H₅ | H | H | H |
| C₂H₅ | C₂H₅ | H | H | H |
| CH₃ | CH₃ | H | CH₃ | H |
| C₂H₅ | C₂H₅ | H | CH₃ | H |
| CH₃ | C₂H₅ | H | CH₃ | H |
| CH₃ | H | 3-CH₃ | H | H |
| CH₃ | H | 5-CH₃ | H | H |
| CH₃ | Cl | H | H | H |
| C(CH₃)₃ | Cl | H | H | H |
| CH₃ | OCH₃ | H | H | H |
| OCH₃ | OCH₃ | H | H | H |
| OCH₃ | C₂H₅ | H | H | H |
| OC₂H₅ | OC₂H₅ | H | H | H |
| CH₃ | CH₃ | H | H | CH₃ |
| CH₃ | C₂H₅ | H | H | CH₃ |
| C₂H₅ | C₂H₅ | H | H | CH₃ |
| C(CH₃)₃ | H | H | H | CH₃ |
| CH₃ | C₂H₅ | H | H | —⟨phenyl⟩ |
| C₂H₅ | C₂H₅ | H | H | —⟨phenyl⟩ |
| CH₃ | CH₃ | H | H | OCH₃ |
| CH₃ | C₂H₅ | H | H | OCH₃ |
| C₂H₅ | C₂H₅ | H | H | OCH₃ |
| C(CH₃)₃ | H | H | H | OCH₃ |
| CH₃ | CH₃ | H | H | SCH₃ |
| CH₃ | C₂H₅ | H | H | SCH₃ |
| C₂H₅ | C₂H₅ | H | H | SCH₃ |
| C(CH₃)₃ | H | H | H | SCH₃ |
| CH₃ | C₂H₅ | H | H | OC₂H₅ |
| C₂H₅ | C₂H₅ | H | H | OC₂H₅ |
| CH₃ | C₂H₅ | H | H | —O—⟨phenyl⟩ |
| C₂H₅ | C₂H₅ | H | H | —O—⟨phenyl⟩ |
| CH₃ | C₂H₅ | H | H | SC₂H₅ |
| C₂H₅ | C₂H₅ | H | H | SC₂H₅ |
| CH₃ | C₂H₅ | H | H | —S—⟨phenyl⟩ |
| C₂H₅ | C₂H₅ | H | H | —S—⟨phenyl⟩ |
| CH₃ | CH₃ | H | H | Cl |
| CH₃ | C₂H₅ | H | H | Cl |
| C₂H₅ | C₂H₅ | H | H | Cl |
| CH₃ | CH₃ | H | H | Br |
| CH₃ | C₂H₅ | H | H | Br |
| C₂H₅ | C₂H₅ | H | H | Br |
| CH₃ | CH₃ | H | H | N(CH₃)₂ |
| CH₃ | C₂H₅ | H | H | N(CH₃)₂ |
| C₂H₅ | C₂H₅ | H | H | N(CH₃)₂ |

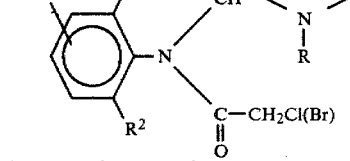  (I e)

| R¹ | R² | R³ | R⁴ | R | X |
|---|---|---|---|---|---|
| CH₃ | CH₃ | H | H | CH₃ | H |
| CH₃ | C₂H₅ | H | H | CH₃ | H |

-continued

| $R^1$ | $R^2$ | $R^3$ | $R^4$ | R | X |
|---|---|---|---|---|---|
| $C_2H_5$ | $C_2H_5$ | H | H | $CH_3$ | H |
| $CH_3$ | $CH_3$ | H | $CH_3$ | $CH_3$ | H |
| $CH_3$ | $C_2H_5$ | H | $CH_3$ | $CH_3$ | H |
| $C_2H_5$ | $C_2H_5$ | H | $CH_3$ | $CH_3$ | H |
| $CH_3$ | $CH_3$ | H | H | $CH_3$ | $CH_3$ |
| $CH_3$ | $C_2H_5$ | H | H | $CH_3$ | $CH_3$ |
| $C_2H_5$ | $C_2H_5$ | H | H | $CH_3$ | $CH_3$ |
| $CH_3$ | $CH_3$ | H | H | $CH_3$ | $OCH_3$ |
| $CH_3$ | $C_2H_5$ | H | H | $CH_3$ | $OCH_3$ |
| $C_2H_5$ | $C_2H_5$ | H | H | $CH_3$ | $OCH_3$ |
| $CH_3$ | $CH_3$ | H | H | $CH_3$ | $SCH_3$ |
| $CH_3$ | $C_2H_5$ | H | H | $CH_3$ | $SCH_3$ |
| $C_2H_5$ | $C_2H_5$ | H | H | $CH_3$ | $SCH_3$ |
| $CH_3$ | $CH_3$ | H | H | $CH_3$ | $C_2H_5$ |
| $CH_3$ | $C_2H_5$ | H | H | $CH_3$ | $C_2H_5$ |
| $C_2H_5$ | $C_2H_5$ | H | H | $CH_3$ | $C_2H_5$ |
| $CH_3$ | $CH_3$ | H | H | $CH_3$ | $C_6H_5$ |
| $CH_3$ | $C_2H_5$ | H | H | $CH_3$ | $C_6H_5$ |
| $C_2H_5$ | $C_2H_5$ | H | H | $CH_3$ | $C_6H_5$ |
| $CH_3$ | $CH_3$ | H | H | $CH_3$ | $C_3H_7$ |
| $CH_3$ | $C_2H_5$ | H | H | $CH_3$ | $C_3H_7$ |
| $C_2H_5$ | $C_2H_5$ | H | H | $CH_3$ | $C_3H_7$ |

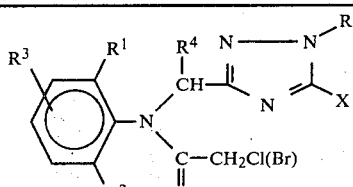 (I f)

| $R^1$ | $R^2$ | $R^3$ | $R^4$ | R | X |
|---|---|---|---|---|---|
| $CH_3$ | $CH_3$ | H | H | $CH_3$ | H |
| $CH_3$ | $C_2H_5$ | H | H | $CH_3$ | H |
| $C_2H_5$ | $C_2H_5$ | H | H | $CH_3$ | H |
| $CH_3$ | $CH_3$ | H | $CH_3$ | $CH_3$ | H |
| $CH_3$ | $C_2H_5$ | H | $CH_3$ | $CH_3$ | H |
| $C_2H_5$ | $C_2H_5$ | H | $CH_3$ | $CH_3$ | H |
| $CH_3$ | $CH_3$ | H | H | $CH_3$ | $CH_3$ |
| $CH_3$ | $C_2H_5$ | H | H | $CH_3$ | $CH_3$ |
| $C_2H_5$ | $C_2H_5$ | H | H | $CH_3$ | $CH_3$ |
| $CH_3$ | $CH_3$ | H | H | $CH_3$ | $OCH_3$ |
| $CH_3$ | $C_2H_5$ | H | H | $CH_3$ | $OCH_3$ |
| $C_2H_5$ | $C_2H_5$ | H | H | $CH_3$ | $OCH_3$ |
| $CH_3$ | $CH_3$ | H | H | $CH_3$ | $SCH_3$ |
| $CH_3$ | $C_2H_5$ | H | H | $CH_3$ | $SCH_3$ |
| $C_2H_5$ | $C_2H_5$ | H | H | $CH_3$ | $SCH_3$ |
| $CH_3$ | $CH_3$ | H | H | $CH_3$ | $C_2H_5$ |
| $CH_3$ | $C_2H_5$ | H | H | $CH_3$ | $C_2H_5$ |
| $C_2H_5$ | $C_2H_5$ | H | H | $CH_3$ | $C_2H_5$ |
| $CH_3$ | $CH_3$ | H | H | $CH_3$ | $C_6H_5$ |
| $CH_3$ | $C_2H_5$ | H | H | $CH_3$ | $C_6H_5$ |
| $C_2H_5$ | $C_2H_5$ | H | H | $CH_3$ | $C_6H_5$ |
| $CH_3$ | $CH_3$ | H | H | $CH_3$ | $C_3H_7$ |
| $CH_3$ | $C_2H_5$ | H | H | $CH_3$ | $C_3H_7$ |
| $C_2H_5$ | $C_2H_5$ | H | H | $CH_3$ | $C_3H_7$ |

Other preferred compounds according to the invention are addition products of acids and those N-diazolylalkylhaloacetanilides of the formula (I) in which A, $R^1$, $R^2$, $R^3$, $R^4$, X and Z have the meanings which have already been mentioned as preferred. The acids which can be added on include, as preferences, hydrogen halide acids (for example hydrobromic acid and, in particular, hydrochloric acid), phosphoric acid, nitric acid, sulphuric acid, monofunctional and bifunctional carboxylic acids and hydroxycarboxylic acids (for example acetic acid, maleic acid, succinic acid, fumaric acid, tartaric acid, citric acid, salicylic acid, sorbic acid and lactic acid) and sulphonic acids (for example p-toluenesulphonic acid and 1,5-naphthalenedisulphonic acid).

Yet other preferred compounds according to the invention are addition products of salts of metals of main groups II to IV and of sub-groups I and II and IV to VIII and those N-diazolylalkyl-haloacetanilides of the formula (I) in which A, $R^1$, $R^2$, $R^3$, $R^4$, X and Z have the meanings which have already been mentioned as preferred. Salts of copper, zinc, manganese, magnesium, tin, iron and nickel are particularly preferred here. Preferred anions of these salts are those which are derived from those acids which lead to physiologically acceptable addition products. In this connection, particularly preferred acids of this type are hydrogen halide acids (for example hydrochloric acid and hydrobromic acid) phosphoric acid, nitric acid and sulphuric acid.

If 2-ethyl-6-methyl-N-(5'-methyl-1',2',4'-oxadiazol-3'-yl-methyl)-aniline and chloroacetyl chloride are used as starting substances in process variant (a), the course of the reaction can be represented by the following equation:

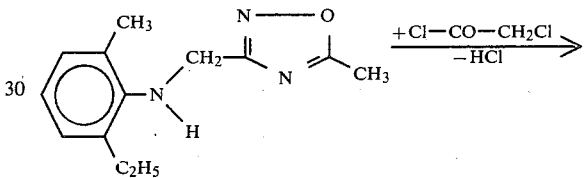

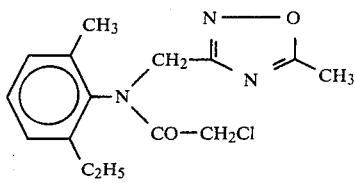

If 2-ethyl-6-methyl-chloroacetanilide and 5-bromomethyl-3-methyl-1,2,4-oxadiazole are used as starting substances in process variant (b), the course of the reaction can be represented by the following equation:

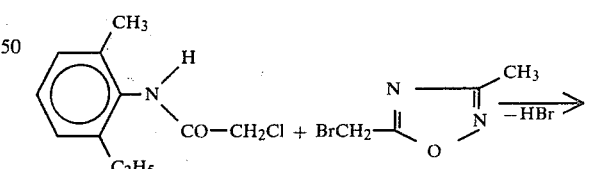

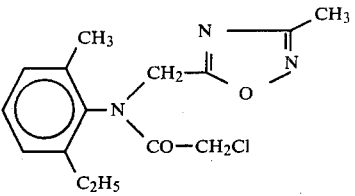

The formula (II) provides a general definition of the N-diazolylalkyl-anilines required as starting substances in carrying out process variant (a) according to the invention. In this formula, A, $R^1$, $R^2$, $R^3$, $R^4$ and X preferably have those meanings which have already been mentioned as preferred in connection with the description of the compounds of the formula (I) according to the invention.

The following compounds may be mentioned as specific examples of compounds of the formula (II):

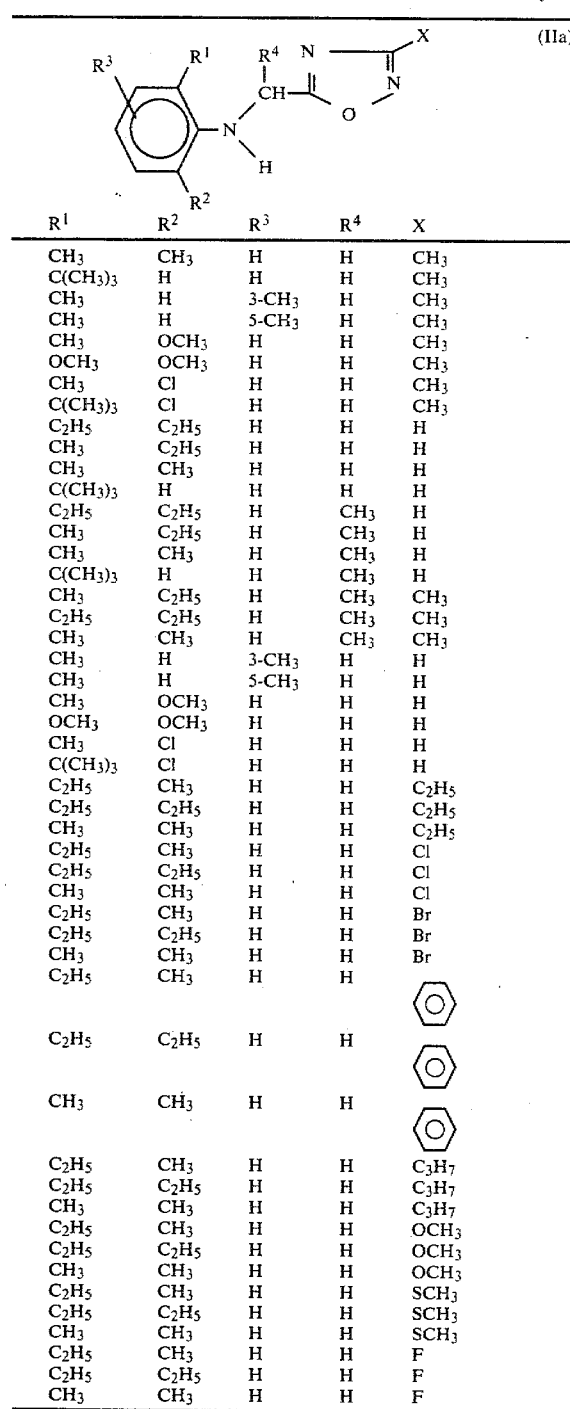
(IIa)

| R¹ | R² | R³ | R⁴ | X |
|---|---|---|---|---|
| CH₃ | CH₃ | H | H | CH₃ |
| C(CH₃)₃ | H | H | H | CH₃ |
| CH₃ | H | 3-CH₃ | H | CH₃ |
| CH₃ | H | 5-CH₃ | H | CH₃ |
| CH₃ | OCH₃ | H | H | CH₃ |
| OCH₃ | OCH₃ | H | H | CH₃ |
| CH₃ | Cl | H | H | CH₃ |
| C(CH₃)₃ | Cl | H | H | CH₃ |
| C₂H₅ | C₂H₅ | H | H | H |
| CH₃ | C₂H₅ | H | H | H |
| CH₃ | CH₃ | H | H | H |
| C(CH₃)₃ | H | H | H | H |
| C₂H₅ | C₂H₅ | H | CH₃ | H |
| CH₃ | C₂H₅ | H | CH₃ | H |
| CH₃ | CH₃ | H | CH₃ | H |
| C(CH₃)₃ | H | H | CH₃ | H |
| CH₃ | C₂H₅ | H | CH₃ | CH₃ |
| C₂H₅ | C₂H₅ | H | CH₃ | CH₃ |
| CH₃ | CH₃ | H | CH₃ | CH₃ |
| CH₃ | H | 3-CH₃ | H | H |
| CH₃ | H | 5-CH₃ | H | H |
| CH₃ | OCH₃ | H | H | H |
| OCH₃ | OCH₃ | H | H | H |
| CH₃ | Cl | H | H | H |
| C(CH₃)₃ | Cl | H | H | H |
| C₂H₅ | CH₃ | H | H | C₂H₅ |
| C₂H₅ | C₂H₅ | H | H | C₂H₅ |
| CH₃ | CH₃ | H | H | C₂H₅ |
| C₂H₅ | CH₃ | H | H | Cl |
| C₂H₅ | C₂H₅ | H | H | Cl |
| CH₃ | CH₃ | H | H | Cl |
| C₂H₅ | CH₃ | H | H | Br |
| C₂H₅ | C₂H₅ | H | H | Br |
| CH₃ | CH₃ | H | H | Br |
| C₂H₅ | CH₃ | H | H | ⟨O⟩ |
| C₂H₅ | C₂H₅ | H | H | ⟨O⟩ |
| CH₃ | CH₃ | H | H | ⟨O⟩ |
| C₂H₅ | CH₃ | H | H | C₃H₇ |
| C₂H₅ | C₂H₅ | H | H | C₃H₇ |
| CH₃ | CH₃ | H | H | C₃H₇ |
| C₂H₅ | CH₃ | H | H | OCH₃ |
| C₂H₅ | C₂H₅ | H | H | OCH₃ |
| CH₃ | CH₃ | H | H | OCH₃ |
| C₂H₅ | CH₃ | H | H | SCH₃ |
| C₂H₅ | C₂H₅ | H | H | SCH₃ |
| CH₃ | CH₃ | H | H | SCH₃ |
| C₂H₅ | CH₃ | H | H | F |
| C₂H₅ | C₂H₅ | H | H | F |
| CH₃ | CH₃ | H | H | F |

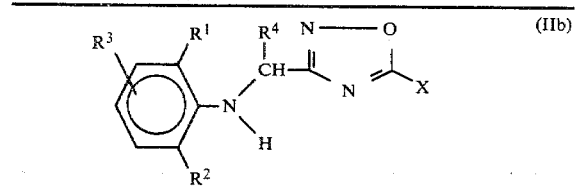
(IIb)

-continued

| R¹ | R² | R³ | R⁴ | X |
|---|---|---|---|---|
| CH₃ | CH₃ | H | H | CH₃ |
| C(CH₃)₃ | H | H | H | CH₃ |
| C₂H₅ | C₂H₅ | H | CH₃ | CH₃ |
| CH₃ | C₂H₅ | H | CH₃ | CH₃ |
| CH₃ | CH₃ | H | CH₃ | CH₃ |
| C(CH₃)₃ | H | H | CH₃ | CH₃ |
| CH₃ | H | 3-CH₃ | H | CH₃ |
| CH₃ | H | 5-CH₃ | H | CH₃ |
| CH₃ | OCH₃ | H | H | CH₃ |
| OCH₃ | OCH₃ | H | H | CH₃ |
| CH₃ | Cl | H | H | CH₃ |
| C(CH₃)₃ | Cl | H | H | CH₃ |
| C₂H₅ | C₂H₅ | H | H | H |
| CH₃ | C₂H₅ | H | H | H |
| CH₃ | CH₃ | H | H | H |
| C(CH₃)₃ | H | H | H | H |
| C₂H₅ | C₂H₅ | H | CH₃ | H |
| CH₃ | C₂H₅ | H | CH₃ | H |
| CH₃ | CH₃ | H | CH₃ | H |
| C(CH₃)₃ | H | H | CH₃ | H |
| CH₃ | H | 3-CH₃ | H | H |
| CH₃ | H | 5-CH₃ | H | H |
| CH₃ | OCH₃ | H | H | H |
| OCH₃ | OCH₃ | H | H | H |
| CH₃ | Cl | H | H | H |
| C(CH₃)₃ | Cl | H | H | H |
| CH₃ | C₂H₅ | H | H | C₂H₅ |
| CH₃ | CH₃ | H | H | C₂H₅ |
| C₂H₅ | C₂H₅ | H | H | n-C₃H₇ |
| CH₃ | C₂H₅ | H | H | n-C₃H₇ |
| CH₃ | CH₃ | H | H | n-C₃H₇ |
| CH₃ | C₂H₅ | H | H | i-C₃H₇ |
| C₂H₅ | C₂H₅ | H | H | i-C₃H₇ |
| CH₃ | CH₃ | H | H | i-C₃H₇ |
| CH₃ | C₂H₅ | H | H | n-C₄H₉ |
| C₂H₅ | C₂H₅ | H | H | n-C₄H₉ |
| CH₃ | CH₃ | H | H | n-C₄H₉ |
| CH₃ | C₂H₅ | H | H | t-C₄H₉ |
| C₂H₅ | C₂H₅ | H | H | t-C₄H₉ |
| CH₃ | CH₃ | H | H | t-C₄H₉ |
| C₂H₅ | C₂H₅ | H | H | ⟨O⟩ |
| CH₃ | C₂H₅ | H | H | ⟨O⟩ |
| CH₃ | CH₃ | H | H | ⟨O⟩ |
| C₂H₅ | C₂H₅ | H | H | Cl |
| CH₃ | C₂H₅ | H | H | Cl |
| CH₃ | CH₃ | H | H | Cl |
| C₂H₅ | C₂H₅ | H | H | OCH₃ |
| CH₃ | C₂H₅ | H | H | OCH₃ |
| C₂H₅ | C₂H₅ | H | H | OC₂H₅ |
| CH₃ | C₂H₅ | H | H | OC₂H₅ |
| C₂H₅ | C₂H₅ | H | H | —O—⟨O⟩ |
| CH₃ | C₂H₅ | H | H | —O—⟨O⟩ |

(IIc)

| R¹ | R² | R³ | R⁴ | X |
|---|---|---|---|---|
| CH₃ | CH₃ | H | H | H |
| CH₃ | C₂H₅ | H | H | H |
| C₂H₅ | C₂H₅ | H | H | H |
| CH₃ | CH₃ | H | CH₃ | H |
| C₂H₅ | C₂H₅ | H | CH₃ | H |
| CH₃ | C₂H₅ | H | CH₃ | H |
| CH₃ | H | 3-CH₃ | H | H |
| CH₃ | H | 5-CH₃ | H | H |

| R¹ | R² | R³ | R⁴ | X |
|---|---|---|---|---|
| CH₃ | Cl | H | H | H |
| C(CH₃)₃ | Cl | H | H | H |
| CH₃ | OCH₃ | H | H | H |
| OCH₃ | OCH₃ | H | H | H |
| OCH₃ | C₂H₅ | H | H | H |
| OC₂H₅ | OC₂H₅ | H | H | H |
| CH₃ | CH₃ | H | H | CH₃ |
| CH₃ | C₂H₅ | H | H | CH₃ |
| C₂H₅ | C₂H₅ | H | H | CH₃ |
| C(CH₃)₃ | H | H | H | CH₃ |
| CH₃ | C₂H₅ | H | H | —⌬ |
| C₂H₅ | C₂H₅ | H | H | —⌬ |
| CH₃ | CH₃ | H | H | OCH₃ |
| CH₃ | C₂H₅ | H | H | OCH₃ |
| C₂H₅ | C₂H₅ | H | H | OCH₃ |
| C(CH₃)₃ | H | H | H | OCH₃ |
| CH₃ | CH₃ | H | H | SCH₃ |
| CH₃ | C₂H₅ | H | H | SCH₃ |
| C₂H₅ | C₂H₅ | H | H | SCH₃ |
| C(CH₃)₃ | H | H | H | SCH₃ |
| CH₃ | C₂H₅ | H | H | OC₂H₅ |
| C₂H₅ | C₂H₅ | H | H | OC₂H₅ |
| CH₃ | C₂H₅ | H | H | —O—⌬ |
| C₂H₅ | C₂H₅ | H | H | —O—⌬ |
| CH₃ | C₂H₅ | H | H | SC₂H₅ |
| C₂H₅ | C₂H₅ | H | H | SC₂H₅ |
| CH₃ | C₂H₅ | H | H | —S—⌬ |
| C₂H₅ | C₂H₅ | H | H | —S—⌬ |
| CH₃ | CH₃ | H | H | Cl |
| CH₃ | C₂H₅ | H | H | Cl |
| C₂H₅ | C₂H₅ | H | H | Cl |
| CH₃ | CH₃ | H | H | Br |
| CH₃ | C₂H₅ | H | H | Br |
| C₂H₅ | C₂H₅ | H | H | Br |
| CH₃ | CH₃ | H | H | N(CH₃)₂ |
| CH₃ | C₂H₅ | H | H | N(CH₃)₂ |
| C₂H₅ | C₂H₅ | H | H | N(CH₃)₂ |

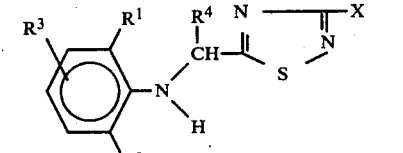

(IId)

| R¹ | R² | R³ | R⁴ | X |
|---|---|---|---|---|
| CH₃ | CH₃ | H | H | H |
| CH₃ | C₂H₅ | H | H | H |
| C₂H₅ | C₂H₅ | H | H | H |
| CH₃ | CH₃ | H | CH₃ | H |
| C₂H₅ | C₂H₅ | H | CH₃ | H |
| CH₃ | C₂H₅ | H | CH₃ | H |
| CH₃ | H | 3-CH₃ | H | H |
| CH₃ | H | 5-CH₃ | H | H |
| CH₃ | Cl | H | H | H |
| C(CH₃)₃ | Cl | H | H | H |
| CH₃ | OCH₃ | H | H | H |
| OCH₃ | OCH₃ | H | H | H |
| OCH₃ | C₂H₅ | H | H | H |
| OC₂H₅ | OC₂H₅ | H | H | H |
| CH₃ | CH₃ | H | H | CH₃ |
| CH₃ | C₂H₅ | H | H | CH₃ |
| C₂H₅ | C₂H₅ | H | H | CH₃ |
| C(CH₃)₃ | H | H | H | CH₃ |
| CH₃ | C₂H₅ | H | H | —⌬ |
| C₂H₅ | C₂H₅ | H | H | —⌬ |
| CH₃ | CH₃ | H | H | OCH₃ |
| CH₃ | C₂H₅ | H | H | OCH₃ |
| C₂H₅ | C₂H₅ | H | H | OCH₃ |
| C(CH₃)₃ | H | H | H | OCH₃ |
| CH₃ | CH₃ | H | H | SCH₃ |
| CH₃ | C₂H₅ | H | H | SCH₃ |
| C₂H₅ | C₂H₅ | H | H | SCH₃ |
| C(CH₃)₃ | H | H | H | SCH₃ |
| CH₃ | C₂H₅ | H | H | OC₂H₅ |
| C₂H₅ | C₂H₅ | H | H | OC₂H₅ |
| CH₃ | C₂H₅ | H | H | —O—⌬ |
| C₂H₅ | C₂H₅ | H | H | —O—⌬ |
| CH₃ | C₂H₅ | H | H | SC₂H₅ |
| C₂H₅ | C₂H₅ | H | H | SC₂H₅ |
| CH₃ | C₂H₅ | H | H | —S—⌬ |
| C₂H₅ | C₂H₅ | H | H | —S—⌬ |
| CH₃ | CH₃ | H | H | Cl |
| CH₃ | C₂H₅ | H | H | Cl |
| C₂H₅ | C₂H₅ | H | H | Cl |
| CH₃ | CH₃ | H | H | Br |
| CH₃ | C₂H₅ | H | H | Br |
| C₂H₅ | C₂H₅ | H | H | Br |
| CH₃ | CH₃ | H | H | N(CH₃)₂ |
| CH₃ | C₂H₅ | H | H | N(CH₃)₂ |
| C₂H₅ | C₂H₅ | H | H | N(CH₃)₂ |

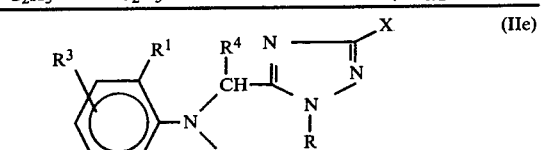

(IIe)

| R¹ | R² | R³ | R⁴ | R | X |
|---|---|---|---|---|---|
| CH₃ | CH₃ | H | H | CH₃ | H |
| CH₃ | C₂H₅ | H | H | CH₃ | H |
| C₂H₅ | C₂H₅ | H | H | CH₃ | H |
| CH₃ | CH₃ | H | CH₃ | CH₃ | H |
| CH₃ | C₂H₅ | H | CH₃ | CH₃ | H |
| C₂H₅ | C₂H₅ | H | CH₃ | CH₃ | H |
| CH₃ | CH₃ | H | H | CH₃ | CH₃ |
| CH₃ | C₂H₅ | H | H | CH₃ | CH₃ |
| C₂H₅ | C₂H₅ | H | H | CH₃ | CH₃ |
| CH₃ | CH₃ | H | H | CH₃ | OCH₃ |
| CH₃ | C₂H₅ | H | H | CH₃ | OCH₃ |
| C₂H₅ | C₂H₅ | H | H | CH₃ | OCH₃ |
| CH₃ | CH₃ | H | H | CH₃ | SCH₃ |
| CH₃ | C₂H₅ | H | H | CH₃ | SCH₃ |
| C₂H₅ | C₂H₅ | H | H | CH₃ | SCH₃ |
| CH₃ | CH₃ | H | H | CH₃ | C₂H₅ |
| CH₃ | C₂H₅ | H | H | CH₃ | C₂H₅ |
| C₂H₅ | C₂H₅ | H | H | CH₃ | C₂H₅ |
| CH₃ | CH₃ | H | H | CH₃ | ⌬ |
| CH₃ | C₂H₅ | H | H | CH₃ | ⌬ |
| C₂H₅ | C₂H₅ | H | H | CH₃ | ⌬ |
| CH₃ | CH₃ | H | H | CH₃ | C₃H₇ |
| CH₃ | C₂H₅ | H | H | CH₃ | C₃H₇ |
| C₂H₅ | C₂H₅ | H | H | CH₃ | C₃H₇ |

-continued

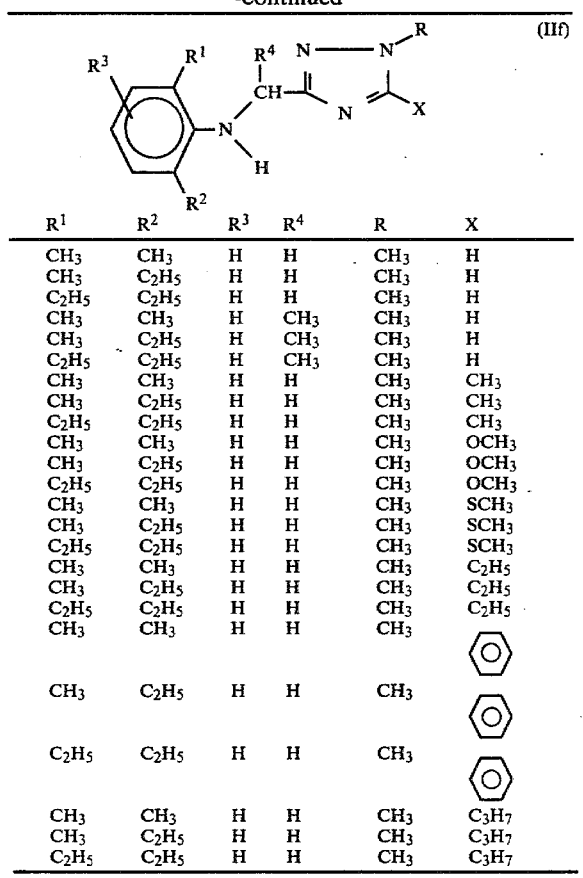

| R¹ | R² | R³ | R⁴ | R | X |
|---|---|---|---|---|---|
| CH₃ | CH₃ | H | H | CH₃ | H |
| CH₃ | C₂H₅ | H | H | CH₃ | H |
| C₂H₅ | C₂H₅ | H | H | CH₃ | H |
| CH₃ | CH₃ | H | CH₃ | CH₃ | H |
| CH₃ | C₂H₅ | H | CH₃ | CH₃ | H |
| C₂H₅ | C₂H₅ | H | CH₃ | CH₃ | H |
| CH₃ | CH₃ | H | H | CH₃ | CH₃ |
| CH₃ | C₂H₅ | H | H | CH₃ | CH₃ |
| C₂H₅ | C₂H₅ | H | H | CH₃ | CH₃ |
| CH₃ | CH₃ | H | H | CH₃ | OCH₃ |
| CH₃ | C₂H₅ | H | H | CH₃ | OCH₃ |
| C₂H₅ | C₂H₅ | H | H | CH₃ | OCH₃ |
| CH₃ | CH₃ | H | H | CH₃ | SCH₃ |
| CH₃ | C₂H₅ | H | H | CH₃ | SCH₃ |
| C₂H₅ | C₂H₅ | H | H | CH₃ | SCH₃ |
| CH₃ | CH₃ | H | H | CH₃ | C₂H₅ |
| CH₃ | C₂H₅ | H | H | CH₃ | C₂H₅ |
| C₂H₅ | C₂H₅ | H | H | CH₃ | C₂H₅ |
| CH₃ | CH₃ | H | H | CH₃ | ⟨O⟩ |
| CH₃ | C₂H₅ | H | H | CH₃ | ⟨O⟩ |
| C₂H₅ | C₂H₅ | H | H | CH₃ | ⟨O⟩ |
| CH₃ | CH₃ | H | H | CH₃ | C₃H₇ |
| CH₃ | C₂H₅ | H | H | CH₃ | C₃H₇ |
| C₂H₅ | C₂H₅ | H | H | CH₃ | C₃H₇ |

The N-diazolylalkyl-anilines of the formula (II) have not hitherto been described in the literature. They are obtained when anilines of the general formula

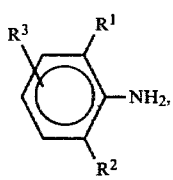

(VI)

in which

R¹, R² and R³ have the meanings stated above, are reacted with diazolylalkyl derivatives of the general formula

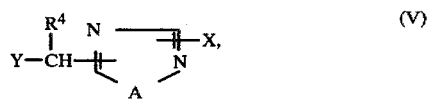

(V)

in which

A, R⁴, X and Y have the meanings stated above, in the presence of an acid-binding agent and if appropriate in the presence of a diluent.

The anilines of the formula (VI) required as starting substances in the preparation of the N-diazolyl-alkyl-anilines of the formula (II) are generally known compounds of organic chemistry. Examples which may be mentioned are: aniline, 2-methylaniline, 2-ethylaniline, 2-isopropylaniline, 2-sec.-butylaniline, 2-tert.-butylaniline, 2,6-dimethylaniline, 2,3-dimethylaniline, 2,5-dimethylaniline, 3,5-dimethylaniline, 2,6-diethylaniline, 2-ethyl-6-methylaniline, 2,3,4-trimethylaniline, 2,4,6-trimethylaniline, 2,4,5-trimethylaniline, 2-ethyl-4,6-dimethylaniline, 2,6-diethyl-4-methylaniline, 2,6-diisopropyl-4-methylaniline, 2,3,5-trimethylaniline, 2,3,6-trimethylaniline, 2-methyl-6-chloroaniline, 2-tert.-butyl-6-chloroaniline, 2-methoxy-6-methylaniline, 2,6-dimethoxyaniline, 2-methoxy-6-ethylaniline, and 2,6-diethoxyaniline.

Any of the customary acid acceptors can be used as acid-binding agents in the preparation of the N-diazolylalkyl-anilines of the formula (II). Alkali metal carbonates, such as potassium carbonate or sodium carbonate, are preferably used.

Any of the customary inert organic solvents can be employed as diluents in the preparation of the N-diazolylalkyl-anilines of the formula (II). Dimethylformamide and toluene are preferably used.

The reaction temperatures can be varied within a substantial range in the preparation of the N-diazolylalkyl-anilines of the formula (II) by the above process. In general, the reaction is carried out between 0° C. and 180° C., preferably between 20° C. and 160° C.

In general, the anilines of the formula (VI) and the diazolylalkyl derivatives of the formula (V) are employed in equimolar amounts in the preparation of the N-diazolylalkyl-anilines of the formula (II) by the above process. However, it is also possible to employ one of the components, preferably the aniline of the formula (VI), in excess. Working up and isolation of the reaction products are effected by customary methods (see also the preparative examples).

The formulae (IIIa) and (IIIb) provide general definitions of the halogenoacetic acid chlorides and bromides and anhydrides also to be used as starting substances for process variant (a) according to the invention. In these formulae, Z preferably represents chlorine, bromine or iodine.

The haloacetic acid chlorides and bromides and anhydrides of the formulae (IIIa) and (IIIb) are generally known compounds of organic chemistry. Examples which may be mentioned are: chloroacetyl chloride, bromoacetyl chloride, iodoacetyl chloride and the corresponding bromides and anhydrides.

The formula (IV) provides a general definition of the haloacetanilides required as starting substances in carrying out process variant (b) according to the invention. In this formula, R¹, R², R³ and Z preferably have those meanings which have already been mentioned as preferred in connection with the description of the substances of the formula (I) according to the invention.

The haloacetanilides of the formula (IV) are generally known, or they can be obtained in a generally known manner, by reacting corresponding anilines with a haloacetic acid chloride or bromide or anhydride of the formulae (IIIa) and (IIIb) in the presence of an inert organic solvent, for example toluene or dimethylformamide, if appropriate in the presence of an acid-binding agent, for example potassium carbonate or triethylamine, at temperatures between 0° C. and 100° C. (see also the preparative examples given later). Examples which may be mentioned are the chloroacetanilides and bromoacetanilides of the above-mentioned anilines of the formula (VI).

The formula (V) provides a general definition of the diazolylalkyl derivatives also to be used as starting substances for process variant (b) according to the invention. In this formula, A, $R^4$ and X preferably have those meanings which have already been mentioned as preferred in connection with the description of the substances of the formula (I) according to the invention. Y preferably represents chlorine, bromine or the mesylate or tosylate radical.

The diazolyl derivatives of the formula (V) are known (see, inter alia, German Offenlegungsschriften (German Published Specifications) Nos. 1,915,495 and 2,054,342, U.S. Pat. Nos. 3,211,742 and 3,264,318 and Bull. Soc. Chim. Belges 73, (1964) 793) or they can be obtained in a generally known manner by the processes described in the literature. The following compounds may be mentioned as specific examples of compounds of the formula (V):

$$Y-CH_2 \underset{O}{\overset{N \longrightarrow X}{\underset{\parallel}{\diagdown}} N} \quad (Va)$$

| X | Y | X | Y |
|---|---|---|---|
| CH₃ | Cl(Br) | ⟨O⟩ | Cl(Br) |
| H | Cl(Br) | C₃H₇ | Cl(Br) |
| C₂H₅ | Cl(Br) | OCH₃ | Cl(Br) |
| Cl | Cl(Br) | | |

$$Y-CH_2 \underset{N}{\overset{N \longrightarrow O}{\underset{\parallel}{\diagdown}} X} \quad (Vb)$$

| X | Y | X | Y |
|---|---|---|---|
| CH₃ | Cl(Br) | Cl | Cl(Br) |
| H | Cl(Br) | OCH₃ | Cl(Br) |
| C₂H₅ | Cl(Br) | OC₂H₅ | Cl(Br) |
| n-C₃H₇ | Cl(Br) | —O—⟨O⟩ | Cl(Br) |
| i-C₃H₇ | Cl(Br) | —⟨O⟩ | Cl(Br) |

$$Y-CH_2 \underset{N}{\overset{N \longrightarrow S}{\underset{\parallel}{\diagdown}} X} \quad (Vc)$$

| X | Y | X | Y |
|---|---|---|---|
| H | Cl(Br) | OC₂H₅ | Cl(Br) |
| CH₃ | Cl(Br) | —O—⟨O⟩ | Cl(Br) |
| ⟨O⟩ | Cl(Br) | SC₂H₅ | Cl(Br) |
| OCH₃ | Cl(Br) | S—⟨O⟩ | Cl(Br) |
| SCH₃ | Cl(Br) | | |

$$Y-CH_2 \underset{N}{\overset{N \longrightarrow N-R}{\underset{\parallel}{\diagdown}} X} \quad (Vd)$$

| X | R | Y |
|---|---|---|
| CH₃ | CH₃ | Cl(Br) |

Preferred diluents for the reaction according to process variant (a) are inert organic solvents. These include, as preferences, ketones, such as diethyl ketone, and in particular acetone and methyl ethyl ketone; nitriles, such as propionitrile, and in particular acetonitrile; ethers, such as tetrahydrofuran or dioxan; aliphatic and aromatic hydrocarbons, such as petroleum ether, benzene, toluene or xylene; halogenated hydrocarbons, such as methylene chloride, carbon tetrachloride, chloroform or chlorobenzene; and esters, such as ethyl acetate.

If appropriate, process variant (a) according to the invention can be carried out in the presence of an acid-binding agent (hydrogen chloride acceptor). Any of the customary acid-binding agents can be used here. These include, as preferences, organic bases, such as tertiary amines, for example triethylamine, or pyridine, and furthermore inorganic bases, for example alkali metal hydroxides and alkali metal carbonates.

The reaction temperatures can be varied within a substantial range in carrying out process variant (a) according to the invention. In general, the reaction is carried out at from 0° C. to 120° C., preferably from 20° C. to 100° C.

In carrying out process variant (a) according to the invention, 1 to 1.5 moles of haloacetylating agent and 1 to 1.5 moles of acid-binding agent are preferably employed per mole of the compound of the formula (II). Isolation of the compounds of the formula (I) is effected in the customary manner.

Possible diluents for the reaction according to process variant (b) are all the inert, water-immiscible, organic solvents. These include, as preferences, ethers, such as diethyl ether; aromatic hydrocarbons, such as benzene, toluene or xylene; halogenated hydrocarbons, such as methylene chloride, carbon tetrachloride, chloroform or chlorobenzene; and esters, such as ethyl acetate.

The reaction, according to the invention, of process variant (b) is carried out in the presence of an acid-binding agent. Any of the customary acid-binding agents can be used here. These include, as preferences, inorganic bases, for example alkali metal hydroxides and alkali metal carbonates, for example sodium or potassium hydroxide and sodium or potassium carbonate.

The reaction temperatures can be varied within a substantial range in carrying out process variant (b) according to the invention. In general, the reaction is carried out at from −70° C. to +100° C., preferably from −20° C. to +80° C.

In carrying out process variant (b) according to the invention, 1 to 1.5 moles of diazolyl-alkyl derivative of the formula (V) are preferably employed per mole of halogenoacetanilide of the formula (IV). Isolation of the compounds of the formula (I) is effected in the customary manner.

In a preferred embodiment, the reaction, according to the invention, of process variant (b) is carried out in a two-phase system, for example aqueous sodium hydroxide solution or potassium hydroxide solution/toluene or methylene chloride, if appropriate with the addition of 0.1–1 mole of a phase transfer catalyst, for example an ammonium or phosphonium compound, benzyl-dodecyl-dimethyl-ammonium chloride (Zephirol) and triethyl-benzyl-ammonium chloride being mentioned as examples (see also the preparative examples given later in this text).

The compounds of the formula (I) according to the invention, whether prepared by process variant (a) or by process variant (b), can be converted into acid addition salts and metal salt complexes.

The following acids are preferably used for the preparation of physiologically acceptable acid addition salts of the compounds of the formula (I): hydrogen halide acids (for example hydrobromic acid and, in particular, hydrochloric acid), phosphoric acid, nitric acid, sulphuric acid, monofunctional and bifunctional carboxylic acids and hydroxycarboxylic acids (for example acetic acid, maleic acid, succinic acid, fumaric acid, tartaric acid, citric acid, salicyclic acid, sorbic acid and lactic acid), and sulphonic acids (for example p-toluenesulphonic acid and 1,5-naphthalenedisulphonic acid).

The acid addition salts of the compounds of the formula (I) can be obtained in a simple manner by customary salt formation methods, for example by dissolving a compound of the formula (I) in a suitable inert solvent and adding the acid, for example hydrochloric acid, and can be isolated in a known manner, for example by filtration, and if appropriate purified by washing with an inert organic solvent.

Salts of metals of main groups II to IV and of subgroups I and II and IV to VIII are preferably used for the preparation of metal salt complexes of the compounds of the formula (I), examples of metals which may be mentioned being copper, zinc, manganese, magnesium, tin, iron and nickel.

Preferred anions of the salts are those which are derived from the following acids: hydrogen halide acids (for example hydrochloric acid and hydrobromic acid), phosphoric acid, nitric acid and sulphuric acid.

The metal salt complexes of compounds of the formula (I) can be obtained in a simple manner by customary processes, for example by dissolving the metal salt in alcohol, for example ethanol, and adding the solution to the compound of the formula (I). Metal salt complexes can be purified in a known manner, for example by filtration, isolation and, if appropriate, by recrystallization.

The active compounds according to the invention influence plant growth and can therefore be used as defoliants, desiccants, agents for destroying broad-leaved plants, germination inhibitors and, especially, as weedkillers. By "weeds" in the broadest sense there are meant plants growing in places where they are not desired.

Whether the compounds according to the invention act as total herbicides or selective herbicides depends essentially on the amount used.

The active compounds according to the present invention may be used, for example, to combat the following plants:

dicotyledon weeds of the genera Sinapis, Lepidium, Galium, Stellaria, Matricaria, Anthemis, Galinsoga, Chenopodium, Urtica, Senecio, Amaranthus, Portulaca, Xanthium, Convolvulus, Ipomea, Polygonum, Sesbania, Ambrosia, Cirsium, Carduus, Sonchus, Rorippa, Rotala, Lindernia, Lamium, Veronica, Abutilon, Emex, Datura, Viola, Galeopsis, Papaver, Centaurea and Solanum; and monocotyledon weeds of the genera Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoira, Fimbristylis, Sagittaria, Eleocharis, Scirpus, Paspalum, Ischaemum, Sphenoclea, Dactyloctenium, Agrostis, Alopecurus and Apera.

The active compounds according to the present invention may be used, for example, as selective herbicides in the following cultures:

dicotyledon cultures of the genera Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita; and monocotyledon cultures of the genera Oryza, Zea, Triticum, Hordeum, Avena, Secale, Sorghum, Panicum, Saccharum, Ananas, Asparagus and Allium.

However, the use of the active compounds according to the invention is in no way restricted to these genera but also embraces other plants, in the same way.

Depending on the concentrations, the compounds can be used for the total combating of weeds, for example on industrial terrain and railway tracks and on paths and squares with or without trees. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cacao plantations, soft fruit plantings and hopfields, and for the selective combating of weeds in annual cultures.

In addition to a very good action against graminaceous weeds, the active compounds according to the invention also exhibit, in particular, a good herbicidal action on broad-leaved weeds. It is possible to use the active compounds according to the invention selectively, preferably in maize, groundnut, beet, soyabean, cotton, rice and other varieties of cereal.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations may be produced in known manner, for example by mixing the active compounds with extenders, that is to say liquid or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention, as such or in the form of their formulations, can also be used, for combating weeds, as mixtures with other herbicides, finished formulations or tank mixing being possible. Mixtures with other active compounds, such as fungicides, insecticides, acaricides, nematicides, bird repellents, growth factors, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules, They may be used in the customary manner, for example by watering, spraying, atomising or scattering.

The active compounds according to the invention can be applied either before or after emergence of the plants. They are preferably used before emergence of the plants, that is to say by the pre-emergence method. They can also be incorporated into the soil before sowing.

The amount of active compound used can vary within a substantial range. It depends essentially on the nature of the desired effect. In general, the amounts used are from 0.1 to 10 kg of active compound per hectare, preferably from 0.1 to 5 kg/ha.

The present invention also provides a herbicidal composition containing as active ingredient a compound of the present invention in admixture with a solid diluent or carrier or in admixture with a liquid diluent or carrier containing a surface-active agent.

The present invention also provides a method of combating weeds which comprises applying to the weeds, or to a habitat thereof, a compound of the present invention alone or in the form of a composition containing as active ingredient a compound of the present invention in admixture with a diluent or carrier.

The present invention further provides crops protected from damage by weeds by being grown in areas in which immediately prior to and/or during the time of the growing a compound of the present invention was applied alone or in admixture with a diluent or carrier.

It will be seen that the usual methods of providing a harvested crop may be improved by the present invention.

The herbicidal activity of the compounds of this invention is illustrated by the following biotest Example.

In this Example, the compounds according to the present invention are each identified by the number (given in brackets) of the corresponding preparative Example, which will be found later in this specification.

The known comparison compound is identified as follows:

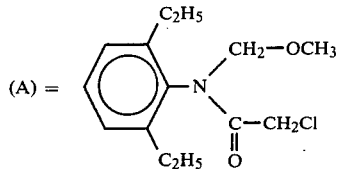

(2,6-diethyl)-N-methoxymethyl-chloroacetanilide.

EXAMPLE A

Pre-emergence test
Solvent: 5 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

Seeds of the test plants were sown in normal soil and, after 24 hours, watered with the preparation of the active compound. It was expedient to keep constant the amount of water per unit area. The concentration of the active compound in the preparation was of no importance, only the amount of active compound applied per unit area being decisive. After three weeks, the degree of damage to the plants was determined in % damage in comparison to the development of the untreated control. The figures denoted:

0% = no action (like untreated control)
100% = total destruction

In this test, active compounds (1), (2), (3) and (4) exhibited a better selective activity than substance (A) known from the prior art.

PREPARATIVE EXAMPLES

EXAMPLE 1

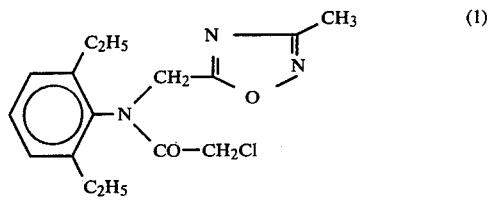

Process variant (a)

8.7 g (0.035 mol) of 2,6-diethyl-N-(3'-methyl-1',2',4'-oxadiazol-5'-yl-methyl)-aniline and 3 g (0.037 mol) of pyridine were heated to the boil in 100 ml of dry tetrahydrofuran. 4.1 g (0.036 mol) of chloroacetyl chloride were then added dropwise, while stirring. After 15 minutes, the entire reaction mixture was concentrated in vacuo and water was added to the residue. The crystals thereby precipitated were filtered off and recrystallized from a little ethyl acetate. 9.4 g (83% of theory) of 2,6-diethyl-N-(3'-methyl-1',2',4'-oxadiazol-5'-yl-methyl)chloroacetanilide of melting point 70°–72° C. were obtained.

PREPARATION OF THE STARTING MATERIAL (II-1)

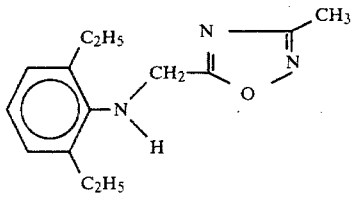

36.8 g (0.25 mol) of 2,6-diethylaniline, 13.8 g (0.1 mol) of powdered potassium carbonate and 13 g (0.1 mol) of 5-chloromethyl-3-methyl-1,2,4-oxadiazole were heated to 100° C. in 25 ml of dimethylformamide for 5 hours, while stirring. Thereafter, the inorganic salt was filtered off, the filtrate was poured onto 100 ml of water and the mixture was extracted with methylene chloride. The organic phase was dried over sodium sulphate and concentrated by distilling off the solvent in vacuo. The only residue was distilled under a high vacuum. 12.2 g (50% of theory) of 2,6-diethyl-N-(3'-methyl-1',2',4'-oxadiazol-5'-yl-methyl)-aniline of boiling point 145° C./0.05 mm Hg were obtained.

EXAMPLE 2

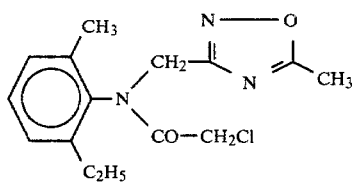

Process variant (a)

2.3 g (0.02 mol) of chloroacetyl chloride were slowly added dropwise to a boiling mixture of 4.6 g (0.02 mol) of 2-ethyl-6-methyl-N-(5'-methyl-1',2',4'-oxadiazol-3'-yl-methyl)-aniline and 2 g (0.025 mol) of pyridine in 100 ml of dry tetrahydrofuran. After 15 minutes, the reaction mixture was concentrated in vacuo, water was added and the mixture was extracted with methylene chloride. The organic phase was dried over sodium sulphate and concentrated by distilling off the solvent in vacuo. The residue was made to crystallize by trituration with petroleum ether. 5 g (81% of theory) of 2-ethyl-6-methyl-N-(5'-methyl-1',2',4'-oxadiazol-3'-yl-methyl)-chloroacetanilide of melting point 69°–72° C. were obtained.

PREPARATION OF THE STARTING MATERIAL (II-2)

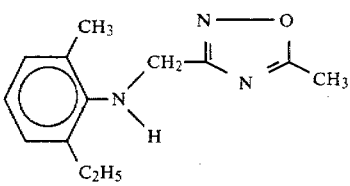

13 g (0.1 mol) of 3-chloromethyl-5-methyl-1,2,4-oxadiazole were added dropwise to a mixture of 27 g (0.2 mol) of 2-ethyl-6-methyl-aniline and 13.8 g (0.1 mol) of potassium carbonate at 100° C., while stirring. The reaction mixture was subsequently stirred at 100° C. for 6 hours and then poured onto water. The mixture was extracted with methylene chloride and the organic phase was dried over sodium sulphate and concentrated by distilling off the solvent in vacuo. The residue was distilled under a high vacuum. 5.2 g (22.5% of theory) of 2-ethyl-6-methyl-N-(5'-methyl-1',2',4'-oxadiazol-3'-yl-methyl)-aniline of boiling point 132° C./0.2 mm Hg and with a melting point of 54°–55° C. were obtained.

Those compounds listed in Table 1 were obtained in a corresponding manner.

TABLE 1

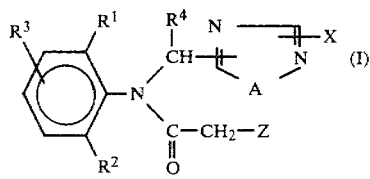

| Example No. | $R^1$ | $R^2$ | $R^3$ | $R^4$ | Z | A | Melting point (°C.) or refractive index |
|---|---|---|---|---|---|---|---|
| 3 | $CH_3$ | $C_2H_5$ | H | H | Cl | (N—O, $CH_3$, N) | Oil |
| 4 | $C_2H_5$ | $C_2H_5$ | H | H | Cl | (N—O, N, $CH_3$) | 91–92 |
| 5 | $C_2H_5$ | $C_2H_5$ | H | H | Cl | (N—O, N, $C_2H_5$) | 39–41 |

TABLE 1-continued

Structure (I):
$R^3$, $R^1$ on phenyl ring; N-CH($R^4$)-A-ring(N=X,N); N-C(=O)-CH$_2$-Z; $R^2$ on phenyl.

| Example No. | $R^1$ | $R^2$ | $R^3$ | $R^4$ | Z | A | Melting point (°C.) or refractive index |
|---|---|---|---|---|---|---|---|
| 6 | CH$_3$ | C$_2$H$_5$ | H | H | Cl | oxadiazole-C$_3$H$_7$-n | viscous oil |
| 7 | CH$_3$ | C$_2$H$_5$ | H | H | Cl | oxadiazole-C$_6$H$_5$ | viscous oil |
| 8 | CH$_3$ | C$_2$H$_5$ | H | H | Cl | thiadiazole-OCH$_3$ | viscous oil |
| 9 | CH$_3$ | CH$_3$ | H | H | Cl | thiadiazole-OCH$_3$ | viscous oil |
| 10 | C$_2$H$_5$ | C$_2$H$_5$ | H | H | Cl | thiadiazole-OCH$_3$ | viscous oil |
| 11 | CH$_3$ | C$_2$H$_5$ | H | H | Cl | thiadiazole-SCH$_3$ | $n_D^{20}$ = 1.6012 |
| 12 | C$_2$H$_5$ | C$_2$H$_5$ | H | H | Cl | thiadiazole-SCH$_3$ | $n_D^{20}$ = 1.6073 |
| 13 | t-C$_4$H$_9$ | H | H | H | Cl | thiadiazole-SCH$_3$ | $n_D^{20}$ = 1.5732 |
| 14 | CH$_3$ | C$_2$H$_5$ | H | H | Cl | thiadiazole-SC$_2$H$_5$ | viscous oil |
| 15 | CH$_3$ | C$_2$H$_5$ | H | H | Cl | thiadiazole-OC$_2$H$_5$ | viscous oil |
| 16 | CH$_3$ | CH$_3$ | H | H | Cl | thiadiazole-OC$_2$H$_5$ | viscous oil |
| 17 | C$_2$H$_5$ | C$_2$H$_5$ | H | H | Cl | thiadiazole-OC$_2$H$_5$ | viscous oil |
| 18 | t-C$_4$H$_9$ | H | H | H | Cl | thiadiazole-OC$_2$H$_5$ | viscous oil |
| 19 | CH$_3$ | CH$_3$ | H | H | Cl | oxadiazole-C$_6$H$_5$ | viscous oil |
| 20 | C$_2$H$_5$ | C$_2$H$_5$ | H | H | Cl | oxadiazole-C$_6$H$_5$ | viscous oil |
| 21 | t-C$_4$H$_9$ | H | H | H | Cl | oxadiazole-C$_6$H$_5$ | viscous oil |
| 22 | CH$_3$ | CH$_3$ | H | H | Cl | isoxazole-CH$_3$ | 87–88° C. |
| 23 | CH$_3$ | CH$_3$ | H | H | Cl | oxadiazole-C$_2$H$_5$ | $n_D^{20}$ = 1.5439 |

TABLE 1-continued

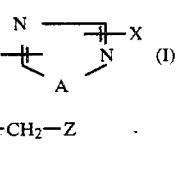

| Example No. | R¹ | R² | R³ | R⁴ | Z | A (with N=N-X ring) | Melting point (°C.) or refractive index |
|---|---|---|---|---|---|---|---|
| 24 | CH₃ | C₂H₅ | H | H | Cl | N—O, C₂H₅ | $n_D^{20} = 1.5409$ |
| 25 | C(CH₃)₃ | H | H | H | Cl | N—O, CH₃ (oxime type) | 120–121 |
| 26 | CH₃ | C₂H₅ | H | H | Cl | N—S, O—C₆H₅ | viscous oil |
| 27 | CH₃ | CH₃ | H | H | Cl | N—S, O—C₆H₅ | viscous oil |
| 28 | C₂H₅ | C₂H₅ | H | H | Cl | N—S, O—C₆H₅ | viscous oil |
| 29 | CH₃ | CH₃ | H | H | Cl | N—O, C₃H₇—n | viscous oil |
| 30 | C₂H₅ | C₂H₅ | H | H | Cl | N—O, C₃H₇—n | viscous oil |
| 31 | C(CH₃)₃ | H | H | H | Cl | N—O, C₃H₇—n | viscous oil |
| 32 | C₂H₅ | C₂H₅ | H | H | Cl | N—S, S—C₂H₅ | viscous oil |
| 33 | CH₃ | CH₃ | H | H | Cl | N—S, S—CH₃ | 55 |
| 34 | CH₃ | CH₃ | H | H | Cl | N—O, CH₃ | 94 |
| 35 | CH₃ | H | H | H | Cl | N—O, CH₃ | 78 |
| 36 | C(CH₃)₃ | H | H | H | Cl | N—O, CH₃ | viscous oil |
| 37 | CH₃ | H | 5-CH₃ | H | Cl | N—O, CH₃ | 94 |
| 38 | CH₃ | H | 3-CH₃ | H | Cl | N—O, C₂H₅ | viscous oil |
| 39 | CH₃ | H | 5-CH₃ | H | Cl | N—O, C₂H₅ | viscous oil |
| 40 | C(CH₃)₃ | H | H | H | Cl | N—O, C₂H₅ | viscous oil |
| 41 | CH₃ | Cl | H | H | Cl | N—O, CH₃ | viscous oil |

TABLE 1-continued $$\text{(I)}$$
Structure: R³, R¹ on phenyl ring with N attached; N bonded to CH(R⁴)–CH=(A)–[N=X–N ring]; N also bonded to C(=O)–CH₂–Z; R² on phenyl.

| Example No. | R¹ | R² | R³ | R⁴ | Z | A (N═X ring) | Melting point (°C.) or refractive index |
|---|---|---|---|---|---|---|---|
| 42 | CH₃ | Cl | H | H | Cl | N—O ring with C₂H₅ | viscous oil |

The starting materials of the formula (II) listed in Table 2 below were obtained by the process described in the foregoing specification, and in a manner corresponding to that described in Examples 1 and 2.

TABLE 2

$$\text{(II)}$$
Structure: R³, R¹ on phenyl; N–H; N bonded to CH(R⁴)–CH=(A)–[N=X–N ring]; R² on phenyl.

| Example No. | R¹ | R² | R³ | R⁴ | A (N═X ring) | Physical constant |
|---|---|---|---|---|---|---|
| (II-3) | CH₃ | C₂H₅ | H | | N—O, CH₃ | boiling point 130–40° C./0.1 mm Hg |
| (II-4) | C₂H₅ | C₂H₅ | H | H | N—O, CH₃ | melting point: 78–80° C. |
| (II-5) | C₂H₅ | C₂H₅ | H | H | N—O, C₂H₅ | boiling point 180–88° C./0.1 mm Hg |
| (II-6) | CH₃ | C₂H₅ | H | H | N—O, C₃H₇-n | viscous oil |
| (II-7) | CH₃ | C₂H₅ | H | H | N—O, phenyl | viscous oil |
| (II-8) | C₂H₅ | C₂H₅ | H | H | N—O, OC₂H₅ | viscous oil |
| (II-9) | CH₃ | C₂H₅ | H | H | N—S, OCH₃ | viscous oil |
| (II-10) | CH₃ | CH₃ | H | H | N—S, OCH₃ | viscous oil |
| (II-11) | C₂H₅ | C₂H₅ | H | H | N—S, OCH₃ | viscous oil |
| (II-12) | CH₃ | C₂H₅ | H | H | N—S, SCH₃ | boiling point 155–160° C./0.1 mm |
| (II-13) | t-C₄H₉ | C₂H₅ | H | H | N—S, SCH₃ | boiling point 220° C./0.1 mm |

TABLE 2-continued

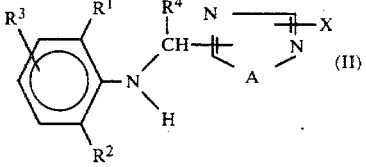

| Example No. | R¹ | R² | R³ | R⁴ | A | Physical constant |
|---|---|---|---|---|---|---|
| (II-14) | CH₃ | C₂H₅ | H | H | (N—S, OC₂H₅) | boiling point 200° C./0,08 mm |
| (II-15) | CH₃ | C₂H₅ | H | H | (N—S, SC₂H₅) | viscous oil |
| (II-16) | CH₃ | CH₃ | H | H | (N—CH₃, O) | boiling point 110–13° C./0.2 mm Hg |
| (II-17) | CH₃ | CH₃ | H | H | (N—O, C₂H₅) | $n_D^{20} = 1,5375$ |
| (II-18) | CH₃ | C₂H₅ | H | H | (N—O, C₂H₅) | $n_D^{20} = 1,5348$ |
| (II-19) | C(CH₃)₃ | H | H | H | (N—CH₃, O) | melting point 85–92° C. |

The starting materials of the formula (IV) listed in Table 3 below were obtained by known processes.

TABLE 3

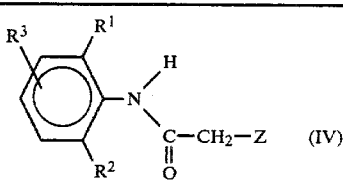

| Example No. | R¹ | R² | R³ | Z | Melting point (°C.) |
|---|---|---|---|---|---|
| (IV-1) | CH₃ | CH₃ | H | Cl | 148 |
| (IV-2) | C₂H₅ | C₂H₅ | H | Cl | 133 |
| (IV-3) | i-C₃H₇ | H | H | Cl | 79 |
| (IV-4) | tert.-C₄H₉ | H | H | Cl | 96 |
| (IV-5) | C₂H₅ | H | H | Cl | 103 |
| (IV-6) | CH₃ | H | H | Cl | 109 |
| (IV-7) | CH₃ | H | 3-CH₃ | Cl | 135 |
| (IV-8) | CH₃ | H | 5-CH₃ | Cl | 154 |
| (IV-9) | CH₃ | CH₃ | 4-CH₃ | Cl | 177 |
| (IV-10) | C₂H₅ | CH₃ | 4-CH₃ | Cl | 134 |
| (IV-11) | sec.-C₄H₉ | H | H | Cl | Oil |
| (IV-12) | H | H | H | Cl | 132 |

It will be understood that the specification and examples are illustrative, but not limitative of the present invention and that other embodiments within the spirit and scope of the invention will suggest themselves to those skilled in the art.

What is claimed is:

1. N-Diazolylalkyl-haloacetanilide of the formula

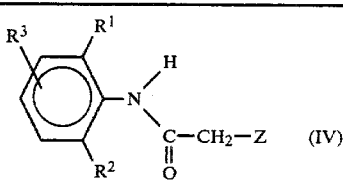

wherein

A is oxygen wherein

R is hydrogen or alkyl with 1 to 4 carbon atoms,

R¹ is hydrogen or alkyl with 1 to 4 carbon atoms,

R² is hydrogen, alkyl with 1 to 4 carbon atoms, alkoxy with 1 to 4 carbon atoms or fluorine, chlorine or bromine, R³ is hydrogen, alkyl with 1 to 4 carbon atoms, alkoxy with 1 to 4 carbon atoms or fluorine, chlorine or bromine, R⁴ is hydrogen or alkyl with 1 to 4 carbon atoms, X is hydrogen, alkyl with 1 to 4 carbon atoms, fluorine, chlorine or bromine, alkoxy with 1 to 4 carbon atoms, alkylthio with 1 to 4 carbon atoms, haloalkyl with 1 or 2 carbon atoms and up to 5 halogen atoms selected individually from fluorine, chlorine and bromine, alkenyl with 2 to 4 carbon atoms, alkynyl with 2 to 4 carbon atoms, alkoxycarbonyl with 1 to 4 carbon atoms in the alkoxy group dialkylamino with 1 to 4 carbon atoms in each alkyl moiety, cyano, phenyl, substituted phenyl, phenoxy, substituted phenoxy, phenylthio or substituted phenylthio, the substituents for the phenyl, phenoxy and phenylthio moieties being individually selected from halogen and alkyl with 1 or 2 carbon atoms, and Z is chlorine, bromine or iodine,
and in which the diazolyl radical is bonded via a carbon atom, and acid addition salts thereof.

2. N-Diazolylalkyl-haloacetanilide compound as claimed in claim 1 wherein $R^1$ is hydrogen.

3. N-Diazolylalkyl-haloacetanilide compound as claimed in claim 1 wherein $R^1$ is alkyl or alkoxy of up to 4 carbon atoms.

4. N-Diazolylakyl-haloacetanilide compound as claimed in claim 1 wherein $R^2$ and $R^3$ are individually selected from hydrogen, alkyl of up to 4 carbon atoms, or chlorine.

5. N-Diazolylalkyl-haloacetanilide compound as claimed in claim 1 wherein $R^4$ is hydrogen.

6. N-Diazolylalkyl-haloacetanilide compound as claimed in claim 1 wherein $R^4$ is alkyl of up to 4 carbon atoms.

7. N-Diazolylalkyl-haloacetanilide compound as claimed in claim 1 wherein X is hydrogen.

8. N-Diazolylalkyl-haloacetanilide compound as claimed in claim 1 wherein X is alkyl with up to 4 carbon atoms.

9. N-Diazolylalkyl-haloacetanilide compound as claimed in claim 1 wherein X is fluorine, chlorine, or bromine.

10. N-Diazolylalkyl-haloacetanilide compound as claimed in claim 1 wherein X is alkoxy or alkylthio with up to 4 carbon atoms.

11. N-Diazolylalkyl-haloacetanilide compound as claimed in claim 1 wherein X is haloalkyl with up to 2 carbon atoms and up to 5 identical or different halogen atoms selected from fluorine, chlorine and bromine.

12. N-Diazolylalkyl-haloacetanilide compound as claimed in claim 1 wherein X is alkenyl or alkynyl with up to 4 carbon atoms.

13. N-Diazolylalkyl-haloacetanilide compound as claimed in claim 1 wherein X is alkoxycarbonyl with up to 4 carbon atoms in the alkoxy moiety.

14. N-Diazolylalkyl-haloacetanilide compound as claimed in claim 1 wherein X is dialkylamino with up to 4 carbon atoms in the alkyl moiety.

15. N-Diazolylalkyl-haloacetanilide compound as claimed in claim 1 wherein X is cyano.

16. N-Diazolylalkyl-haloacetanilide compound as claimed in claim 1 wherein X is phenyl, substituted phenyl, phenoxy, substituted phenoxy, phenylthio, the substituents being selected from fluorine, chlorine, bromine, and alkyl with 1 or 2 carbon atoms.

17. N-Diazolylalkyl-haloacetanilide compound as claimed in claim 1 wherein Z is chlorine.

18. N-Diazolylalkyl-haloacetanilide compound as claimed in claim 1 wherein
A is oxygen, sulphur or the grouping >NR wherein R is hydrogen or alkyl with 1 to 4 carbon atoms,
$R^1$ is hydrogen, alkyl or alkoxy with 1 to 4 carbon atoms,
$R^2$ and $R^3$ are individually selected from hydrogen, alkyl or alkoxy with from 1 to 4 carbon atoms, fluorine, bromine or chlorine,
$R^4$ is hydrogen or alkyl with 1 to 4 carbon atoms,
X is hydrogen, alkyl with 1 to 4 carbon atoms, alkoxy with 1 to 4 carbon atoms, alkylthio with 1 to 4 carbon atoms, alkoxycarbonyl with 1 to 4 carbon atoms in the alkoxy group, alkenyl or alkynyl with from 2 to 4 carbon atoms, fluorine, chlorine, bromine, haloalkyl with up to 2 carbon atoms and up to 5 identical or different halogen atoms, dialkylamino with 1 to 4 carbon atoms in each alkyl moiety, cyano, phenyl, substituted phenyl, phenoxy, substituted phenoxy, phenylthio, substituted phenylthio, the substituents being selected from halogen and alkyl with from 1 or 2 carbon atoms, and
Z is chlorine, bromine or iodine.

19. N-Diazolylalkyl-haloacetanilide compound as claimed in claim 1 in the form of an acid addition salt wherein the acid is selected from hydrogen halide acids, phosphoric acid, nitric acid, sulfuric acid, mono- and bi-functional carboxylic and hydroxy-carboxylic acids, and sulfonic acids.

20. N-Diazolylalkyl-haloacetanilide compounds as claimed in claim 1 wherein
A is oxygen,
$R^1$ is hydrogen or alkyl with 1-4 carbon atoms,
$R^2$ is hydrogen, alkyl with 1-4 carbon atoms or chlorine,
$R^3$ is hydrogen or alkyl with 1-4 carbon atoms,
$R^4$ is hydrogen,
X is hydrogen, alkyl with 1-4 carbon atoms, alkoxy with 1-4 carbon atoms, alkylthio with 1-4 carbon atoms, chlorine, phenyl or phenoxy, and
Z is chlorine.

21. N-Diazolylalkyl-haloacetanilide compound designated 2,6-diethyl-N-(3'-methyl-1',2'-4'-oxadiazol-5'-yl-methyl)-chloracetanilide.

22. N-diazolylalkyl-haloacetanilide compound designated 2-ethyl-6-methyl-N-(5'-methyl-1',2',4'-oxadiazol-3'-yl-methyl)-chloracetanilide.

23. N-diazolylalkyl-haloacetanilide compound designated 2-ethyl-6-methyl-N-(3'-methyl-1',2',4'-oxadiazol-5'-yl-methyl)-chloracetanilide.

24. N-diazolylalkyl-haloacetanilide compound designated 2,6-diethyl-N-(5'-methyl-1',2',4'-oxadiazol-3'-yl-methyl)-chloracetanilide.

25. N-diazolylalkyl-haloacetanilide compound designated 2,6-diethyl-N-(5'-ethyl-1',2',4'-oxadiazol-3'-yl-methyl)-chloracetanilide.

26. Herbicidal composition comprising a herbicidally acceptable carrier and, in herbicidally effective amounts, an N-diazolylalkyl-haloacetanilide compound as claimed in claim 1.

27. Method of combating weeds which method comprises applying to these weeds, or ther habitat a herbicidally effective amount of an N-diazolylalkyl-haloacetanilide compound as claimed in claim 1.

28. Method as claimed in claim 27 wherein said N-diazolylaklyl-haloacetanilide compound is selected from
2,6-diethyl-N-(3'-methyl-1'2',4-oxadiazol-5'-yl-methyl)-chloracetanilide
2-ethyl-6-methyl-N-(5'-methyl-1,2,4-oxadiazol-3'-yl-methyl)-chloracetanilide
2-ethyl-6-methyl-N-(3'-methyl-1',2',4'-oxadiazol-5'-yl-methyl)-chloracetanilide
2,6-diethyl-N-(5'-methyl-1',2',4'-oxadiazol-3'-yl-methyl)-chloracetanilide and
2,6-diethyl-N-(5'-ethyl-1',2',4'-oxadiazol-3-'yl-methyl)-chloracetanilide.

29. Method as claimed in claim 27 wherein said compound is applied at a dosage of 0.1 to 10 kg per hectare.

30. Method as claimed in claim 27 wherein said compound is applied at a dosage of 0.1 to 5 kg per hectare.

* * * * *